United States Patent
Sorondo

(10) Patent No.: US 9,686,926 B2
(45) Date of Patent: Jun. 27, 2017

(54) **CHIA (*SALVIA HISPANICA* L.) VARIETY SAHI ALBA 914**

(71) Applicant: TFSB, LLC, Dover, DE (US)

(72) Inventor: Agustin Sorondo, Buenos Aires (AR)

(73) Assignee: TFSB, LLC, Dover, DE (US)

( * ) Notice: Subject to any disclaimer, the term of this patent is extended or adjusted under 35 U.S.C. 154(b) by 439 days.

(21) Appl. No.: 13/872,235

(22) Filed: Apr. 29, 2013

(65) Prior Publication Data

US 2014/0325694 A1    Oct. 30, 2014

(51) Int. Cl.
*A01H 5/10*     (2006.01)

(52) U.S. Cl.
CPC .................... *A01H 5/10* (2013.01)

(58) Field of Classification Search
None
See application file for complete search history.

(56) References Cited

U.S. PATENT DOCUMENTS

| | | | | |
|---|---|---|---|---|
| 5,739,409 | A * | 4/1998 | Fischer | C07K 14/43 435/320.1 |
| 7,312,376 | B2 * | 12/2007 | Apuya | C12N 15/8243 435/320.1 |
| 8,586,831 | B2 * | 11/2013 | Hildebrand | A01H 5/12 435/410 |
| 2013/0007909 | A1 | 1/2013 | Hildebrand et al. | |

OTHER PUBLICATIONS

Agin, K. 2009, WholeFoods Magzine, Sowing the Seeds of Wellness.*
Cahill et al 2002, The Journal of Heredity 93(1): 52-55.*
Yan et al 2007 Plant Cell Tiss. Organ Cult. 88: 175-184.*
Salba Smart, "Salba Chia Nutrition" http://www.salbasmart.com/history-of-salba [retrieved from the Internet on Sep. 30, 2013].

* cited by examiner

*Primary Examiner* — David H Kruse
(74) *Attorney, Agent, or Firm* — McKee, Voorhees & Sease, PLC

(57) ABSTRACT

According to the invention, there is provided a novel chia (*Salvia hispanica* L.) variety, designated Sahi Alba 914 which is independent of photoperiod, in contrast to its closest relatives. This allows the variety to be sown earlier, and to be grown at higher latitudes such as the United States. This invention thus relates to the seeds of chia (*Salvia hispanica* L.) variety Sahi Alba 914, to the plants of chia (*Salvia hispanica* L.) variety Sahi Alba 914, to plant parts of chia (*Salvia hispanica* L.) variety Sahi Alba 914, to methods for producing a chia (*Salvia hispanica* L.) variety by crossing the chia (*Salvia hispanica* L.) variety Sahi Alba 914 with another chia (*Salvia hispanica* L.) variety, and to methods for producing a chia (*Salvia hispanica* L.) variety containing in its genetic material one or more backcross conversion traits or transgenes and to the backcross conversion chia (*Salvia hispanica* L.) plants and plant parts produced by those methods.

27 Claims, No Drawings

CHIA (SALVIA HISPANICA L.) VARIETY SAHI ALBA 914

FIELD OF THE INVENTION

The present invention relates to the field of plant breeding. In particular, this invention relates to a new chia (*Salvia hispanica* L.) variety designated Sahi Alba 914.

BACKGROUND OF THE INVENTION

The nutrient dense make-up of chia makes it a good way to boost daily nutrition, with thousands of years of use to back up its efficacy. As early as 3500 BC athletes consumed chia as a super fuel for energy and endurance. Salba chia is the richest whole food source of Omega-3 fatty acids (ALA) and fiber found in nature on a gram for gram basis. Every 15 g serving provides over 3,400 mg of Omega-3s (ALA) and over 5,000 mg of dietary fiber. Chia has less than 1 g net carbohydrate per serving.

Salba chia is incredibly nutrient dense. Gram for gram, Salba chia has six times more calcium than whole milk, three times more iron than spinach, and fifteen times more magnesium than broccoli. It is all-natural, has no trans-fat, is gluten free, has almost no carbohydrates and is a whole food.

Salba Chia Gram for Gram provides 325% more fiber than oatmeal, 800% more Omega-3 (ALA) than salmon (EPA/DHA), 30% more antioxidants than blueberries (based on ORAC values), 1500% more magnesium than broccoli, and 200% more potassium than bananas.

Currently, chia is commercially grown in tropical and subtropical areas, e.g., areas in Argentina, Bolivia, Colombia, Mexico and Peru where latitude are ranged from 20° 55'N to 25° 05'S. However, in higher latitudes like Choele-Choele, (39° 11'S) Argentina and Tucson (32° 14'N), Ariz., USA, chia plants do not produce seeds since the seeds are killed by frost before they mature.

Efforts for improving chia seed production has largely been focused on selecting or breeding domesticated varieties of chia strains. However, lack of reliable sources of chia limits the potential to bring chia to the market as a new commercial crop. Therefore, there is a need to generate new chia strains that would allow chia seeds to be produced in much of the United States and other temperate regions.

The foregoing examples of the related art and limitations related therewith are intended to be illustrative and not exclusive. Other limitations of the related art will become apparent to those of skill in the art upon a reading of the specification.

SUMMARY OF THE INVENTION

According to the invention, there is provided a novel chia (*Salvia hispanica* L.) variety, designated Sahi Alba 914. This invention thus relates to the seeds of chia variety Sahi Alba 914, to the plants of chia variety Sahi Alba 914, to plant parts of chia variety Sahi Alba 914, to methods for producing a chia variety produced by crossing the chia variety Sahi Alba 914 with another chia variety, and to methods for producing a chia variety containing in its genetic material one or more backcross conversion traits or transgenes and to the backcross conversion chia plants and plant parts produced by those methods. This invention also relates to chia varieties and plant parts derived from chia variety Sahi Alba 914, to methods for producing other varieties derived from chia variety Sahi Alba 914 and to the chia varieties and their parts derived by the use of those methods. This invention further relates to chia variety seeds, plants and plant parts produced by crossing the chia variety Sahi Alba 914 or a backcross conversion of Sahi Alba 914 with another chia variety.

DETAILED DESCRIPTION OF THE INVENTION

Definitions

In the description and tables that follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Allele. Any of one or more alternative forms of a genetic sequence. In a diploid cell or organism, the two alleles of a given sequence typically occupy corresponding loci on a pair of homologous chromosomes.

Alter/modulate. The utilization of up-regulation, down-regulation, or gene silencing.

Backcrossing. A process in which a breeder crosses progeny back to one of the parental genotypes one or more times. Commonly used to introduce one or more locus conversions from one genetic background into another.

Breeding. The genetic manipulation of living organisms.

BU/A. Bushels per Acre. The seed yield in bushels/acre is the actual yield of the grain at harvest.

Cell. Cell as used herein includes a plant cell, whether isolated, in tissue culture or incorporated in a plant or plant part.

Cotyledon. A cotyledon is a type of seed leaf. The cotyledon contains the food storage tissues of the seed.

Cross-pollination. Fertilization by the union of two gametes from different plants.

Diploid. A cell or organism having two sets of chromosomes.

Embryo. The embryo is the small plant contained within a mature seed.

Emergence. This score indicates the ability of the seed to emerge when planted 3" deep in sand at a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

$F_\#$. The "F" symbol denotes the filial generation, and the # is the generation number, such as $F_1$, $F_2$, $F_3$, etc.

Gene. As used herein, "gene" refers to a unit of inheritance corresponding to DNA or RNA that code for a type of protein or for an RNA chain that has a function in the organism.

Gene Silencing. The interruption or suppression of the expression of a gene at the level of transcription or translation.

Genotype. Refers to the genetic constitution of a cell or organism.

Haploid. A cell or organism having one set of the two sets of chromosomes in a diploid.

Hypocotyl. A hypocotyl is the portion of an embryo or seedling between the cotyledons and the root. Therefore, it can be considered a transition zone between shoot and root.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A defined segment of DNA.

Lodging Resistance. Lodging is rated on a scale of 1 to 9. A score of 9 indicates erect plants. A score of 5 indicates plants are leaning at a 45° angle in relation to the ground and a score of 1 indicates plants are lying on the ground.

Maturity Date. Plants are considered mature when 95% of the pods have reached their mature color. The number of days are calculated either from August 31 or from the planting date.

Nucleic Acid. An acidic, chainlike biological macromolecule consisting of multiple repeat units of phosphoric acid, sugar and purine and pyrimidine bases.

Pedigree. Refers to the lineage or genealogical descent of a plant.

Pedigree Distance. Relationship among generations based on their ancestral links as evidenced in pedigrees. May be measured by the distance of the pedigree from a given starting point in the ancestry.

Percent Identity. Percent identity as used herein refers to the comparison of the homozygous alleles of two varieties. Percent identity is determined by comparing a statistically significant number of the homozygous alleles of two developed varieties. For example, a percent identity of 90% between variety 1 and variety 2 means that the two varieties have the same allele at 90% of their loci.

Percent Similarity. Percent similarity as used herein refers to the comparison of the homozygous alleles of a chia variety such as chia cultivar S100104 with another plant, and if the homozygous allele of chia cultivar S100104 matches at least one of the alleles from the other plant, then they are scored as similar. Percent similarity is determined by comparing a statistically significant number of loci and recording the number of loci with similar alleles as a percentage. A percent similarity of 90% between chia cultivar S100104 and another plant means that chia cultivar S100104 matches at least one of the alleles of the other plant at 90% of the loci.

Phenotypic Score. The Phenotypic Score is a visual rating of general appearance of the variety. All visual traits are considered in the score including healthiness, standability, appearance, and freedom of disease. Ratings are scored from 1 being poor to 9 being excellent.

Plant. As used herein, the term "plant" includes reference to an immature or mature whole plant, including a plant from which seed, grain, or anthers have been removed. Seed or embryo that will produce the plant is also considered to be the plant.

Plant Height. Plant height is taken from the top of the soil to the top node of the plant and is measured in centimeters.

Plant Parts. As used herein, the term "plant parts" (or a chia plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Progeny. As used herein, includes an $F_1$ chia plant produced from the cross of two chia plants where at least one plant includes chia cultivar S100104 and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

Protein Percent. Chia seeds contain a considerable amount of protein. Protein is generally measured by NIR spectrophotometry and is reported on an as is percentage basis.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Seed Protein Peroxidase Activity. Seed protein peroxidase activity refers to a chemical taxonomic technique to separate cultivars based on the presence or absence of the peroxidase enzyme in the seed coat. There are two types of chia cultivars; those having high peroxidase activity (dark red color) and those having low peroxidase activity (no color).

Seed Yield (Bushels/Acre). The yield in bushels/acre is the actual yield of the grain at harvest.

Seeds Per Pound. Chia seeds vary in seed size; therefore, the number of seeds required to make up one pound also varies. The number of seeds per pound affect the pounds of seed required to plant a given area and can also impact end uses.

Single Gene Converted (Conversion). Single gene converted (conversion), also known as coisogenic plants, refers to plants which are developed by a plant breeding technique called backcrossing wherein essentially all of the desired morphological and physiological characteristics of a variety are recovered in addition to the single gene transferred into the variety via the backcrossing technique or via genetic engineering.

The development of 'Sahi Alba 914' started with breeding from generic or wild chia and selecting for plants having white seed. There are currently no known public varieties of chia. The breeding method used was a mass bulk of seed, followed by planting and selection for white seed. The first Sahi Alba variety developed in this manner was 'Sahi Alba 911', which is distinguished by having all white seeds, whereas generic or wild chia have a mixture of seed colors, such as black, white, and several different shades of grey. 'Sahi Alba 912' was developed from 'Sahi Alba 911' with the distinction that 'Sahi Alba 912' was selected for white flowers, whereas 'Sahi Alba 911' has violet flowers.

'Sahi Alba 914' was selected from a commercial field of 'Sahi Alba 912' for early flowering plants. The breeding method used was again individual selection with mass conduction. Over a cultivation of 'Sahi Alba 912', a plant was selected that started the flowering period 10 days earlier than the rest of the cultivation. The following year, a seed of this plant was sown 30 days before the sowing date, and 10 days after the flowering started all plants that had not yet flowered were eliminated. This process was repeated during several years until the entire cultivation flowered during the same period. Plants were grown in Jujuy Province, Argentina with the following cycles of selection:

| Cycle | % of early flowering plants |
|---|---|
| 1 | 26 |
| 2 | 54 |
| 3 | 73 |
| 4 | 94 |

-continued

| Cycle | % of early flowering plants |
|---|---|
| 5 | 100 |
| 6 | 100 |

The significance of the early flowering plants is that the early flowering is independent of photoperiod, meaning that the plants can be grown in a wider range of environmental conditions, and specifically at higher latitudes farther from the equator.

Sahi Alba 914 grows in sunlight, medium moisture, and loam to sandy soils. It propagates by seed, and is an open pollinated annual. The plant is herbaceous and upright with simple, opposite, decussate leaves. The leaves are also petiolated, lanceolate-ovate, with two creases at the petiole base. The edge of the leaves is between crenate and serrate.

Flowers have axillary and terminal verticillasters. Flower color is white with monopetalous tubular corolla. A persistent calyx which is tubular, bulgy, striate and trilobate is present. The flowers have two anthers with longitudinal dehiscence. The ovary is superior, bicarpelar, and tetralocular on a nectariferous disc. The style is glabrous, with glandular base, and bifid.

The fruit is schizocarp. At maturity it divides into four individual fruits or mericarps inside the calyx. The fruit has oleaginous albumen and underdeveloped endosperm.

'Sahi Alba 914' has been observed for 4 generations of reproduction and during the seed increase period and is stable and uniform. Variants appear in 'Sahi Alba 914' at a frequency of about 1 in 500. These variants have violet flowers or do not flower at all, but are identical to 'Sahi Alba 914' in all other characteristics as described in Table 1. These variants are commercially acceptable and predictable.

TABLE 1

Variety Description Information and Comparison Data

| Trait | Variety Data Sahi Alba 914 Average (Mean) | Comparison Variety Data Sahi Alba 912 Average (Mean) |
|---|---|---|
| Number of Chromosomes (1N) | 6 | 6 |
| Days from emergence to 50% of plants in flower | 54-60 | 61-69 |
| mm Plant Height at Maturity | 1060-1210 | 1140-1300 |
| mm Main Stem Length | 836-986 | 950-1110 |
| mm Width of Leaf | 44 | 45 |
| mm Length of Leaf Including Petiole | 109 | 111 |
| mm Lenth of Petiole | 33 | 33 |
| mm Inflorescence Height from Ground | 836-986 | 950-1110 |
| Number of Petals per Floret | 1 | 1 |
| Number of Anthers per Floret | 2 | 2 |
| Number of Stigmas per Floret | 1 | 1 |
| Number of Seeds per Fruit | 4 | 4 |
| mg Weight per 1000 Seeds | 1100-1400 | 1100-1400 |
| mm Seed Length | 2.15-2.33 | 2.15-2.33 |
| Plant Colors | | |
| Petal Color, Main | White | White |
| DISEASE, Insect and Environment Resistance (Rate from 1 (most susceptible) to 9 (most resistant)) | | |
| Aphids | 8 | 8 |
| Heat | 8 | 8 |
| Cold | 1 | 1 |
| Wind | 6 | 5 |

'Sabi Alba 914' is most similar to proprietary varieties 'Sabi Alba 911' and 'Sabi Alba 912'; however, 'Sabi Alba 914' is independent of the photoperiod, whereas 'Sabi Alba 911' and 'Sabi Alba 912' require the photoperiod.

The difference in photoperiod response allows 'Sabi Alba 914' to be sown earlier than 'Sabi Alba 911' and 'Sabi Alba 912' when grown at the same location, thus avoiding the first frost. Additionally, the independence of photoperiod of 'Sabi Alba 914' allows for 'Sabi Alba 914' to be grown at higher latitudes farther from the equator where no other varieties of chia can be produced.

TABLE 2

Table 2: Comparison of Sahi Alba 914 and its most similar variety, cv. "911 and 912" The table below shows additional differences between 'Sahi Alba 914' and the closest known varieties, proprietary varieties 'Sahi Alba 911' and 'Sahi Alba 912':

| Characteristic | Sahi Alba 911 | Sahi Alba 912 | Sahi Alba 914 |
|---|---|---|---|
| Height (cm) | 92-125 | 114-130 | 106-121 |
| Deviation (%) | 15.4 | 12.6 | — |
| Stems | Quadrangular, grooved, pubescent | Quadrangular, grooved, pubescent | Quadrangular, grooved, pubescent |
| Leaves | Simple, opposite, decussate, petiolated, lanceolate-elliptic, with two crests at the petiole base | Simple, opposite, decussate, petiolated, lanceolate-elliptic, with two crests at the petiole base | Simple, opposite, decussate, petiolated, lanceolate-elliptic, with two crests at the petiole base |
| Edge | Between crenate and serrate | Between crenate and serrate | Between crenate and serrate |
| Leaf width (cm) | 4.4 | 4.5 | 4.4 |
| Leaf length (cm) | 7.5 | 7.8 | 7.6 |
| Petiole (cm) | 3.3 | 3.3 | 3.3 |
| Leaves of the spike stalks | Ovate oblong, 2.5 cm width, 0.5 cm petiole | Ovate oblong, 2.5 cm width, 0.5 cm petiole | Ovate oblong, 2.5 cm width, 0.5 cm petiole |

TABLE 2-continued

Table 2: Comparison of Sahi Alba 914 and its most similar variety, cv. "911 and 912" The table below shows additional differences between 'Sahi Alba 914' and the closest known varieties, proprietary varieties 'Sahi Alba 911' and 'Sahi Alba 912':

| Characteristic | Sahi Alba 911 | Sahi Alba 912 | Sahi Alba 914 |
|---|---|---|---|
| Corolla | Monopetalous, tubular | Monopetalous, tubular | Monopetalous, tubular |
| Calyx | Persistent, tubular, bulgy, striate, trilobate | Persistent, tubular, bulgy, striate, trilobate | Persistent, tubular, bulgy, striate, trilobate |
| Flowers | Bluish violet or violet, only rarely white | White, in at least 95% of cases | White, in at least 95% of cases |
| Inflorescence | Axillary and terminal verticillasters | Axillary and terminal verticillasters | Axillary and terminal verticillasters |
| Length | Main inflorescence: 21.6 cm Secondary inflorescences average: 8.6 cm | Main inflorescence: 19 cm Secondary inflorescences average: 8 cm | Main inflorescence: 22.4 cm Secondary inflorescences average: 8.9 cm |
| Seeds | 4, of 2.15-2.33 mm | 4, of 2.15-2.33 mm | 4, of 2.15-2.33 mm |
| Inner part | Oleaginous albumen, underdeveloped endosperm | Oleaginous albumen, underdeveloped endosperm | Oleaginous albumen, underdeveloped endosperm |
| Stamens | 2, anthers with longitudinal dehiscence | 2, anthers with longitudinal dehiscence | 2, anthers with longitudinal dehiscence |
| Ovary | Superior, bicarpelar and tetralocular, on a nectariferous disc | Superior, bicarpelar and tetralocular, on a nectariferous disc | Superior, bicarpelar and tetralocular, on a nectariferous disc |
| Style | Glabrous, with glandular base and bifid | Glabrous, with glandular base and bifid | Glabrous, with glandular base and bifid |
| Fruit | Schizocarp, at maturity it divides into 4 individual fruits or persistent mericarps inside the calyx | Schizocarp, at maturity it divides into 4 individual fruits or persistent mericarps inside the calyx | Schizocarp, at maturity it divides into 4 individual fruits or persistent mericarps inside the calyx |
| Fertilization | Cross-pollinated and entomophilous | Cross-pollinated and entomophilous | Cross-pollinated and entomophilous |
| Flowering - emergence days | 62-70 | 61-69 | 54-60 |
| Maturity - emergence days | 110-120 | 105-115 | 95-104 |
| Chromosomes | 2n = 12 | 2n = 12 | 2n = 12 |

This invention is also directed to methods for producing a chia (*Salvia hispanica* L.) plant by crossing a first parent chia (*Salvia hispanica* L.) plant with a second parent chia (*Salvia hispanica* L.) plant, wherein the first parent chia (*Salvia hispanica* L.) plant or second parent chia (*Salvia hispanica* L.) plant is the chia (*Salvia hispanica* L.) plant from variety Sahi Alba 914. Further, both the first parent chia (*Salvia hispanica* L.) plant and second parent chia (*Salvia hispanica* L.) plant may be from variety Sahi Alba 914. Therefore, any methods using chia (*Salvia hispanica* L.) variety Sahi Alba 914 are part of this invention, such as selfing, backcrosses, hybrid breeding, and crosses to populations. Plants produced using chia (*Salvia hispanica* L.) variety Sahi Alba 914 as at least one parent are within the scope of this invention.

In one aspect of the invention, methods for developing novel plant types are presented. In one embodiment the specific type of breeding method is pedigree selection, where both single plant selection and mass selection practices are employed. Pedigree selection, also known as the "Vilmorin system of selection," is described in Fehr, Walter; Principles of Variety Development, Volume I, Macmillan Publishing Co., which is hereby incorporated by reference. In chia (*Salvia hispanica* L.) breeding, lines may be selected for certain desired appropriate characteristics. In one embodiment, the pedigree method of breeding is practiced where selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny row the preceding generation.

Using this pedigree method, two parents may be crossed using an emasculated female and a pollen donor (male) to produce $F_1$ offspring or open pollination. As such, methods of removing pollen well known to one of skill in the art, such as misting to wash the pollen off prior to fertilization, may be employed to assure crossing or hybridization. The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

In addition to crossing, selection may be used to identify and isolate new chia (*Salvia hispanica* L.) lines. In chia (*Salvia hispanica* L.) selection, chia (*Salvia hispanica* L.) seeds are planted, the plants are grown and single plant selections are made of plants with desired characteristics.

Seed from the single plant selections may be harvested, separated from seeds of the other plants in the field and re-planted. The plants from the selected seed may be monitored to determine if they exhibit the desired characteristics of the originally selected line. Selection work is preferably continued over multiple generations to increase the uniformity of the new line.

Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding may be used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful varieties produced per unit of input (e.g., per year, per dollar expended, etc.).

In one embodiment, promising advanced breeding lines are thoroughly tested and compared to appropriate standards in environments representative of the commercial target area(s). The best lines are candidates for new commercial varieties; those still deficient in a few traits are used as parents to produce new populations for further selection.

These processes, which lead to the final step of marketing and distribution, usually take several years from the time the first cross or selection is made. Therefore, development of new varieties is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. If a single observation is inconclusive, replicated observations provide a better estimate of its genetic worth.

The goal of chia (*Salvia hispanica* L.) plant breeding is to develop new, unique and superior chia (*Salvia hispanica* L.) varieties. In one embodiment, the breeder initially selects and crosses two or more parental lines, followed by repeated selfing and selection, producing many new genetic combinations. The breeder can theoretically generate billions of different genetic combinations via crossing, selfing and mutations. Preferably, each year the plant breeder selects the germplasm to advance to the next generation. This germplasm may be grown under different geographical, climatic and soil conditions, and further selections are then made, during and at the end of the growing season.

In a preferred embodiment, the development of commercial chia (*Salvia hispanica* L.) varieties requires the development of chia (*Salvia hispanica* L.) varieties, the crossing of these varieties, and the evaluation of the crosses. Pedigree breeding and recurrent selection breeding methods may be used to develop varieties from breeding populations. Breeding programs may combine desirable traits from two or more varieties or various broad-based sources into breeding pools from which varieties are developed by selfing and selection of desired phenotypes. The new varieties may be crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are usually selected. Replicated testing of families, or hybrid combinations involving individuals of these families, often follows in the $F_4$ generation to improve the effectiveness of selection for traits with low heritability. At an advanced stage of inbreeding (e.g., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals may be identified or created by intercrossing several different parents. The best plants may be selected based on individual superiority, outstanding progeny, or excellent combining ability. Preferably, the selected plants are intercrossed to produce a new population in which further cycles of selection are continued.

Backcross breeding has been used to transfer genes for a simply inherited, highly heritable trait into a desirable homozygous variety or line that is the recurrent parent. The source of the trait to be transferred is called the donor parent. The resulting plant is expected to have the attributes of the recurrent parent (e.g., variety) and the desirable trait transferred from the donor parent. After the initial cross, individuals possessing the phenotype of the donor parent may be selected and repeatedly crossed (backcrossed) to the recurrent parent. The resulting plant is expected to have the attributes of the recurrent parent (e.g., variety) and the desirable trait transferred from the donor parent.

The single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Chia (*Glycine max*) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Chia, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in chia with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into chia (*Salvia hispanica* L.) varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Variety Development by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Chia (*Salvia hispanica* L.) is an important and valuable vegetable crop. Thus, a continuing goal of chia (*Salvia hispanica* L.) plant breeders is to develop stable, high yielding chia (*Salvia hispanica* L.) varieties that are agronomically sound. To accomplish this goal, the chia (*Salvia hispanica* L.) breeder preferably selects and develops chia (S*alvia hispanica* L.) plants with traits that result in superior varieties.

This invention also is directed to methods for producing a chia (*Salvia hispanica* L.) variety plant by crossing a first parent chia (*Salvia hispanica* L.) plant with a second parent chia (*Salvia hispanica* L.) plant wherein either the first or second parent chia (*Salvia hispanica* L.) plant is a chia (*Salvia hispanica* L.) plant of the line Sahi Alba 914. Further, both first and second parent chia (*Salvia hispanica* L.) plants can come from the variety Sahi Alba 914. Still further, this invention also is directed to methods for producing a variety Sahi Alba 914-derived chia (*Salvia hispanica* L.) plant by crossing variety Sahi Alba 914 with a second chia (*Salvia hispanica* L.) plant and growing the progeny seed, and repeating the crossing and growing steps with the variety Sahi Alba 914-derived plant from 0 to 7 times. Thus, any such methods using the variety Sahi Alba 914 are part of this invention: selfing, backcrosses, hybrid production, crosses to populations, and the like. All plants produced using variety Sahi Alba 914 as a parent are within the scope of this invention, including plants derived from variety Sahi Alba 914. Advantageously, the variety is used in crosses with other, different, varieties to produce first generation ($F_1$) chia (*Salvia hispanica* L.) seeds and plants with superior characteristics.

As used herein, the term plant includes plant cells, plant protoplasts, plant cell tissue cultures from which chia (*Salvia hispanica* L.) plants can be regenerated, plant calli, plant clumps and plant cells that are intact in plants or parts of plants, such as embryos, pollen, ovules, flowers, seeds, roots, anthers, and the like.

As is well known in the art, tissue culture of chia (*Salvia hispanica* L.) can be used for the in vitro regeneration of a chia (*Salvia hispanica* L.) plant. Tissue culture of various tissues of chia (*Salvia hispanica* L.)s and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce chia (Salvia hispanica L.) plants having the physiological and morphological characteristics of variety Sahi Alba 914.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as transgenes. Over the last fifteen to twenty years several methods for producing transgenic plants have been developed, and the present invention, in particular embodiments, also relates to transformed versions of the claimed line.

Plant transformation preferably involves the construction of an expression vector that will function in plant cells. Such a vector may comprise DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed chia (Salvia hispanica L.) plants, using transformation methods as described below to incorporate transgenes into the genetic material of the chia (Salvia hispanica L.) plant(s).

Expression Vectors for Chia (Salvia hispanica L.) Transformation Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990<Hille et al., Plant Mol. Biol. 7:171 (1986). Other selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include .beta.-glucuronidase (GUS), .beta.-galaetesidase, luciferase and chloramphenicol, acetyltransferasef 3. Jefferson, R. A., Plant Mol. Biol. Rep. 5:387 (1987), Teeri et al., EMBO J. 8:343 (1989), Koncz et al., Proc. Natl. Acad. Sci. U.S.A. 84:131 (1987), DeBlock et al., EMBO J. 3:1681 (1984).

Recently, in vivo methods for visualizing GUS activity that do not require destruction of plant tissue have been made available. Molecular Probes publication 2908, Imagene Green™, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters

Genes included in expression vectors preferably are driven by nucleotide sequence comprising a regulatory element, for example, a promoter. Several types of promoters are now well known in the transformation arts, as are other regulatory elements that can be used alone or in combination with promoters.

As used herein, promoter includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive promoter" is a promoter which is active under most environmental conditions.

A. Inducible Promoters

An inducible promoter is operably linked to a gene for expression in chia (*Salvia hispanica* L.). Optionally, the inducible promoter is operably linked to a nucleotide sequence encoding a signal sequence which is operably linked to a gene for expression in chia (*Salvia hispanica* L.). With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Meft et al., PNAS 90:4567-4571 (1993)); In2 gene from maize which responds to benzenesulfonamide herbicide safeners (Hershey et al., Mol. Gen. Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter may be operably linked to a gene for expression in chia (*Salvia hispanica* L.) or the constitutive promoter may operably linked to a nucleotide sequence encoding a signal sequence which is operably linked to a gene for expression in chia (*Salvia hispanica* L.).

Many different constitutive promoters can be utilized in the instant invention. Exemplary constitutive promoters include, but are not limited to, the promoters from plant viruses such as the 35S promoter from CaMV (Odell et al., Nature 313:810-812 (1985) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT application WO96/30530.

C. Tissue-Specific or Tissue-Preferred Promoters

A tissue-specific promoter may be operably linked to a gene for expression in chia (*Salvia hispanica* L.). Optionally, the tissue-specific promoter is operably linked to a nucleotide sequence encoding a signal sequence which is operably linked to a gene for expression in chia (*Salvia hispanica* L.). Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zml3 (Guerrero et al., Mol. Gen. Genetics 244:161-168 (1993)) or a microspore-preferred promoter such as that from apg (Twell et al., Sex. Plant Reprod. 6:217-224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., Structure and Organization of Two Divergent Alpha-Amylase Genes from Barley, Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is chia (*Salvia hispanica* L.). In another preferred embodiment, the biomass of interest is seed. For transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons may involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. Tomato encodes a protein kinase); Mindrinos et al., Cell 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* .alpha.-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung chia (*Salvia hispanica* L.) calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of tachyolesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf Taylor et al., Abstract #497, Seventh Intl Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb at al., Bio/Technology 10:1436 (1992). The cloning and characterization of a gene which encodes a chia (*Salvia hispanica* L.) endopolygalacturonase-inhibiting protein is described by Toubart et al., Plant J. 2:367 (1992).

R. A development-arrestive protein produced in nature by a plant. For example, Logemann et al., Bioi/Technology 10:305 (1992), have shown that transgenic plants expressing the barley ribosome-inactivating gene have an increased resistance to fungal disease.

S. A chia (*Salvia hispanica* L.) mosaic potyvirus (LMV) coat protein gene introduced into chia in order to increase its resistance to LMV infection. See Dinant et al., Molecular Breeding. 1997, 3: 1, 75-86.

2. Genes that Confer Resistance to an Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase PAT bar genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada at al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Accl-S1, Accl-S2 and Accl-S3 genes described by Marshall et al., Theor. Appl. Genet. 83:435 (1992).

C. A herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995.

Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Increased iron content of the chia (*Salvia hispanica* L.), for example by transforming a plant with a chia ferritin gene as described in Goto et al., Acta Horticulturae. 2000, 521, 101-109. Parallel to the improved iron content enhanced growth of transgenic chia (*Salvia hispanica* L.)s was also observed in early development stages.

B. Decreased nitrate content of leaves, for example by transforming a chia (*Salvia hispanica* L.) with a gene coding for a nitrate reductase. See for example Curtis et al., Plant Cell Report. 1999, 18: 11, 889-896.

C. Increased sweetness of the chia (*Salvia hispanica* L.) by transferring a gene coding for monellin that elicits a flavor sweeter than sugar on a molar basis. See Penarrubia et al., Biotechnology. 1992, 10: 5, 561-564.

D. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

E. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis* .alpha.-amylase), Elliot et al., Plant Molec. Biol. 21:515 (1993) (nucleotide sequences of tomato invertase genes), Sogaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

4. Genes that Control Male-Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Chia (*Salvia hispanica* L.) Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R.

and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., Science 227:1229 (1985). Curtis et al., Journal of Experimental Botany. 1994, 45: 279, 1441-1449, Torres et al., Plant cell Tissue and Organic Culture. 1993, 34: 3, 279-285, Dinant et al., Molecular Breeding. 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 .mu.m. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, January), 165-169 (1993), Aragao, F. J. L., et al. Plant Mol. Biol. 20(2, October), 357-359 (1992), Aragao, F. J. L., et al. Pl. Cell. Rep. 12(9, July), 483-490 (1993). Aragao, Theor. Appl. Genet. 93: 142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992).

Another method for physical delivery of DNA to plants is sonication of target cells. Zhang et al., Bio/Technology 9:996 (1991). Alternatively, liposome or spheroplast fusion has been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine has also been reported. Hain et al., Mol. Gen. Genet. 199:161 (1985) and Draper et al., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994). See also Chupean et al., Biotechnology. 1989, 7: 5, 503-508.

Following transformation of chia (*Salvia hispanica* L.) target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic chia (*Salvia hispanica* L.) line. Alternatively, a genetic trait that has been engineered into a particular chia (*Salvia hispanica* L.) variety using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term chia (*Salvia hispanica* L.) plant, variety or chia (*Salvia hispanica* L.) line is used in the context of the present invention, this also includes any gene conversions of that line. The term gene converted plant as used herein refers to those chia (*Salvia hispanica* L.) plants which are developed by a plant breeding technique called backcrossing wherein essentially all of the desired morphological and physiological characteristics of a variety are recovered in addition to the gene transferred into the line via the backcrossing technique. Backcrossing methods can be used with the present invention to improve or introduce a characteristic into the line. The term backcrossing as used herein refers to the repeated crossing of a hybrid progeny back to one of the parental chia (*Salvia hispanica* L.) plants for that line. The parental chia (*Salvia hispanica* L.) plant that contributes the gene for the desired characteristic is termed the nonrecurrent or donor parent. This terminology refers to the fact that the nonrecurrent parent is used one time in the backcross protocol and therefore does not recur. The parental chia (*Salvia hispanica* L.) plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second line (nonrecurrent parent) that carries the single gene of interest to be transferred. The resulting progeny from this cross are then crossed again to the recurrent parent and the process is repeated until a chia (*Salvia hispanica* L.) plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute traits or characteristics in the original line. To accomplish this, a gene or genes of the recurrent variety are modified or substituted with the desired gene or genes from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait or traits to the plant. The exact backcrossing protocol will depend on the characteristics or traits being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected for in the development of a new line but that can be improved by backcrossing techniques. Gene traits may or may not be transgenic, examples of these traits include but are not limited to, herbicide resistance, resistance for bacterial, fungal, or viral disease, insect resistance, enhanced nutritional quality, industrial usage, yield stability, yield enhancement, male sterility, modified fatty acid metabolism, and modified carbohydrate metabolism. These genes are generally inherited through the nucleus. Several of these gene traits are described in U.S. Pat. Nos. 5,777,196; 5,948,957 and 5,969,212, the disclosures of which are specifically hereby incorporated by reference.

Tissue Culture

Further reproduction of the variety can occur by tissue culture and regeneration. Tissue culture of various tissues of chia (Salvia hispanica L.) and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672, and Ibrahim et al., Plant Cell, Tissue and Organ Culture. (1992), 28(2): 139-145. It is clear from the literature that the state of the art is such that these methods of obtaining plants are routinely used and have a very high rate of success. Thus, another aspect of this invention is to provide cells which upon growth and differentiation produce chia (Salvia hispanica L.) plants having the physiological and morphological characteristics of variety Sahi Alba 914.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a chia (Salvia hispanica L.) plant by crossing a first parent chia (Salvia hispanica L.) plant with a second parent chia (Salvia hispanica L.) plant wherein the first or second parent chia (Salvia hispanica L.) plant is a chia (Salvia hispanica L.) plant of variety Sahi Alba 914. Further, both first and second parent chia (Salvia hispanica L.) plants can come from chia (Salvia hispanica L.) variety Sahi Alba 914. Thus, any such methods using chia (Salvia hispanica L.) variety Sahi Alba 914 are part of this invention: selfing, backcrosses, hybrid production, crosses to populations, and the like. All plants produced using chia (Salvia hispanica L.) variety Sahi Alba 914 as at least one parent are within the scope of this invention, including those developed from varieties derived from chia (Salvia hispanica L.) variety Sahi Alba 914. Advantageously, this chia (Salvia hispanica L.) variety could be used in crosses with other, different, chia (Salvia hispanica L.) plants to produce the first generation ($F_1$) chia (Salvia hispanica L.) hybrid seeds and plants with superior characteristics. The variety of the invention can also be used for transformation where exogenous genes are introduced and expressed by the variety of the invention. Genetic variants created either through traditional breeding methods using chia (Salvia hispanica L.) variety Sahi Alba 914 or through transformation of variety Sahi Alba 914 by any of a number of protocols known to those of skill in the art are intended to be within the scope of this invention.

The following describes breeding methods that may be used with chia (Salvia hispanica L.) variety Sahi Alba 914 in the development of further chia (Salvia hispanica L.) plants. One such embodiment is a method for developing variety Sahi Alba 914 progeny chia (Salvia hispanica L.) plants in a chia (Salvia hispanica L.) plant breeding program comprising: obtaining the chia (Salvia hispanica L.) plant, or a part thereof, of variety Sahi Alba 914, utilizing said plant or plant part as a source of breeding material, and selecting a chia (Salvia hispanica L.) variety Sahi Alba 914 progeny plant with molecular markers in common with variety Sahi Alba 914 and/or with morphological and/or physiological characteristics selected from the characteristics listed in Table 1. Breeding steps that may be used in the chia (Salvia hispanica L.) plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method which may be used involves producing a population of chia (Salvia hispanica L.) variety Sahi Alba 914-progeny chia (Salvia hispanica L.) plants, comprising crossing variety Sahi Alba 914 with another chia (Salvia hispanica L.) plant, thereby producing a population of chia (Salvia hispanica L.) plants, which, on average, derive 50% of their alleles from chia (Salvia hispanica L.) variety Sahi Alba 914. A plant of this population may be selected and repeatedly selfed or sibbed with a chia (Salvia hispanica L.) variety resulting from these successive filial generations. One embodiment of this invention is the chia (Salvia hispanica L.) variety produced by this method and that has obtained at least 50% of its alleles from chia (Salvia hispanica L.) variety Sahi Alba 914.

One of ordinary skill in the art of plant breeding would know how to evaluate the traits of two plant varieties to determine if there is no significant difference between the two traits expressed by those varieties. For example, see Fehr and Walt, Principles of Variety Development, p 261-286 (1987). Thus the invention includes chia (Salvia hispanica L.) variety Sahi Alba 914 progeny chia (Salvia hispanica L.) plants comprising a combination of at least two variety Sahi Alba 914 traits selected from the group consisting of those listed in Table 1 or the variety Sahi Alba 914 combination of traits listed above, so that said progeny chia (Salvia hispanica L.) plant is not significantly different for said traits than chia (Salvia hispanica L.) variety Sahi Alba 914 as determined at the 5% significance level when grown in the same environmental conditions. Using techniques described herein, molecular markers may be used to identify said progeny plant as a chia (Salvia hispanica L.) variety Sahi Alba 914 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of chia (*Salvia hispanica* L.) variety Sahi Alba 914 may also be characterized through their filial relationship with chia (*Salvia hispanica* L.) variety Sahi Alba 914, as for example, being within a certain number of breeding crosses of chia (*Salvia hispanica* L.) variety Sahi Alba 914. A breeding cross is a cross made to introduce new genetics into the progeny, and is distinguished from a cross, such as a self or a sib cross, made to select among existing genetic alleles. The lower the number of breeding crosses in the pedigree, the closer the relationship between chia (*Salvia hispanica* L.) variety Sahi Alba 914 and its progeny. For example, progeny produced by the methods described herein may be within 1, 2, 3, 4 or 5 breeding crosses of chia (*Salvia hispanica* L.) variety Sahi Alba 914.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

DEPOSITS

Applicant(s) have made a deposit of at least 2500 seeds of Chia (*Salvia hispanica* L.) Variety Sahi Alba 914 with the American Type Culture Collection (ATCC), Manassas, Va. 20110 USA, ATCC Deposit No. PTA-123789. The seeds deposited with the ATCC were taken from the deposit maintained by the inventor at Paraná 1315, Entrepiso (C1018ADG), Ciudad Autónoma de Buenos Aires, Argentina since prior to the filing date of this application. Access to this deposit will be available during the pendency of the application to the Commissioner of Patents and Trademarks and persons determined by the Commissioner to be entitled thereto upon request. Upon issue of claims, the Applicant(s) will make available to the public, pursuant to 37 CFR 1.808, a deposit of at least 2500 seeds of variety Sahi Alba 914 with the American type Culture Collection (ATCC), 10801 University Boulevard, Manassas, Va. 20110-2209. This deposit of the chia (*Salvia hispanica* L.) variety Sahi Alba 914 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants have no authority to waive any restrictions imposed by law on the transfer of biological material or its transportation in commerce. Applicants do not waive any infringement of their rights granted under this patent or under the Plant Variety Protection Act (7 USC 2321 et seq.).

What is claimed is:

1. A seed of chia (*Salvia hispanica* L.) variety designated Sahi Alba 914, wherein a representative sample of seed of said variety was deposited under ATCC Accession No. PTA-123789.

2. A chia (*Salvia hispanica* L.) plant, or a part thereof, produced by growing the seed of claim 1.

3. A tissue culture of cells produced from the plant of claim 2, wherein said cells of the tissue culture are produced from a plant part selected from the group consisting of embryo, meristematic cell, leaf, cotyledon, hypocotyl, stem, root, root tip, pistil, anther, flower, seed and pollen.

4. A protoplast produced from the plant of claim 2.

5. A protoplast produced from the tissue culture of claim 3.

6. A chia (*Salvia hispanica* L.) plant regenerated from the tissue culture of claim 3, wherein the plant has all of the morphological and physiological characteristics of variety Sahi Alba 914, wherein a representative sample of seed was deposited under ATCC Accession No. PTA-123789.

7. A method for producing a progeny chia (*Salvia hispanica* L.) seed, wherein the method comprises crossing the plant of claim 2 with a different chia (*Salvia hispanica* L.) plant and harvesting the resultant $F_1$ chia (*Salvia hispanica* L.) seed.

8. A $F_1$ progeny chia (*Salvia hispanica* L.) seed produced by the method of claim 7.

9. A progeny chia (*Salvia hispanica* L.) plant, or a part thereof, produced by growing said $F_1$ progeny seed of claim 8.

10. A method of producing a male sterile chia (*Salvia hispanica* L.) plant wherein the method comprises transforming the chia (*Salvia hispanica* L.) plant of claim 2 with a nucleic acid molecule that confers male sterility.

11. A male sterile chia (*Salvia hispanica* L.) plant produced by the method of claim 10.

12. A method for producing an herbicide resistant chia (*Salvia hispanica* L.) plant wherein the method comprises transforming the chia (*Salvia hispanica* L.) plant of claim 2 with a transgene, wherein the transgene confers resistance to an herbicide selected from the group consisting of imidazolinone, sulfonylurea, glyphosate, glufosinate, L-phosphinothricin, triazine and benzonitrile.

13. An herbicide resistant chia (*Salvia hispanica* L.) plant produced by the method of claim 12.

14. A method of producing an insect resistant chia (*Salvia hispanica* L.) plant wherein the method comprises transforming the chia (*Salvia hispanica* L.) plant of claim 2 with a transgene that confers insect resistance.

15. An insect resistant chia (*Salvia hispanica* L.) plant produced by the method of claim 14.

16. The chia (*Salvia hispanica* L.) plant of claim 15 wherein the transgene encodes a *Bacillus thuringiensis* endotoxin.

17. A method of producing a disease resistant chia (*Salvia hispanica* L.) plant wherein the method comprises transforming the chia (*Salvia hispanica* L.) plant of claim 2 with a transgene that confers disease resistance.

18. A disease resistant chia (*Salvia hispanica* L.) plant produced by the method of claim 17.

19. A method of producing a chia (*Salvia hispanica* L.) plant with a value-added trait, wherein the method comprises transforming the chia (*Salvia hispanica* L.) plant of claim 2 with a transgene encoding a protein selected from the group consisting of a ferritin, a nitrate reductase, and a monellin.

20. A chia (*Salvia hispanica* L.) plant with a value-added trait produced by the method of claim 19.

21. A chia (*Salvia hispanica* L.) plant, or a part thereof, having all of the physiological and morphological characteristics of chia (*Salvia hispanica* L.) variety Sahi Alba 914, wherein a representative sample of seed of the variety was deposited under ATCC Accession No. PTA-123789.

22. A method of introducing a desired trait into chia (*Salvia hispanica* L.) variety Sahi Alba 914 wherein the method comprises: a) crossing a Sahi Alba 914 plant grown from Sahi Alba 914 seed, wherein a representative sample of seed was deposited under ATCC Accession No. PTA-123789, with a plant of another chia (*Salvia hispanica* L.) variety that comprises a desired trait to produce $F_1$ progeny plants, wherein the desired trait is selected from the group consisting of male sterility, herbicide resistance, insect resistance, and resistance to bacterial disease, fungal disease, or viral disease; b) selecting one or more progeny plants that have the desired trait to produce selected progeny plants; c) crossing the selected progeny plants with the Sahi Alba 914 plants to produce backcross progeny plants; d) selecting for backcross progeny plants that have the desired trait and all of the physiological and morphological characteristics of chia (*Salvia hispanica* L.) variety Sahi Alba 914 listed in Table 1 to produce selected backcross progeny plants; and e) repeating steps (c) and (d) three or more times in succession to produce selected fourth or higher backcross progeny plants that comprise the desired trait and all of the physiological and morphological characteristics of chia (*Salvia hispanica* L.) variety Sahi Alba 914 listed in Table 1.

23. A chia (*Salvia hispanica* L.) plant produced by the method of claim 22, wherein the plant has the desired trait and all of the physiological and morphological characteristics of chia (*Salvia hispanica* L.) variety Sahi Alba 914 listed in Table 1.

24. The chia (*Salvia hispanica* L.) plant of claim 23, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

25. The chia (*Salvia hispanica* L.) plant of claim 23, wherein the desired trait is insect resistance and the insect resistance is conferred by a transgene encoding a *Bacillus thuringiensis* endotoxin.

26. The chia (*Salvia hispanica* L.) plant of claim 23, wherein the desired trait is male sterility and the trait is conferred by a nucleic acid molecule.

27. A population of chia plants of the plant of claim 2.

* * * * *